United States Patent
Bansal et al.

(10) Patent No.: US 10,413,704 B2
(45) Date of Patent: Sep. 17, 2019

(54) MECHANISM FOR CONTROLLING UNINTENTIONAL MOVEMENT OF COMPONENTS

(71) Applicant: St. Jude Medical, Cardiology Division, Inc., St. Paul, MN (US)

(72) Inventors: Varun Bansal, Plymouth, MN (US); Bradley C. Knippel, Lino Lakes, MN (US); Ryan Cerepak, Champlin, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 26 days.

(21) Appl. No.: 15/308,280

(22) PCT Filed: Jun. 1, 2015

(86) PCT No.: PCT/US2015/033517
§ 371 (c)(1),
(2) Date: Nov. 1, 2016

(87) PCT Pub. No.: WO2015/187547
PCT Pub. Date: Dec. 10, 2015

(65) Prior Publication Data
US 2017/0056624 A1  Mar. 2, 2017

Related U.S. Application Data

(60) Provisional application No. 62/008,222, filed on Jun. 5, 2014.

(51) Int. Cl.
*A61M 25/01* (2006.01)
*A61B 1/00* (2006.01)
*A61M 39/10* (2006.01)

(52) U.S. Cl.
CPC ..... *A61M 25/0136* (2013.01); *A61B 1/00039* (2013.01); *A61M 39/10* (2013.01); *A61M 2039/1038* (2013.01)

(58) Field of Classification Search
CPC .............. A61M 25/0136; A61M 39/10; A61M 2039/1038; A61B 1/00039
See application file for complete search history.

(56) References Cited

U.S. PATENT DOCUMENTS

| | | | |
|---|---|---|---|
| 2,462,603 A * | 2/1949 | Boots | F16B 39/34 238/262 |
| 4,346,703 A * | 8/1982 | Dennehey | A61M 5/14 604/244 |

(Continued)

FOREIGN PATENT DOCUMENTS

| | | |
|---|---|---|
| JP | S60-129941 U | 8/1985 |
| JP | H10-61634 A | 3/1998 |

(Continued)

*Primary Examiner* — Amber R Stiles
(74) *Attorney, Agent, or Firm* — Armstrong Teasdale LLP (57) ABSTRACT

The present disclosure provides a medical device (10) comprising a friction member (30, 48) configured to assist in controlling and/or limiting unintentional and/or undesirable movement between two releasably secured components (18, 28) of the medical device. The releasably secured components may be part of a resistance assembly for holding a medical device actuator (20) in a particular position and/or to improve the ease of which the activator moves into one position versus another position.

12 Claims, 9 Drawing Sheets

(56) References Cited

U.S. PATENT DOCUMENTS

| | | | | |
|---|---|---|---|---|
| 4,629,455 A | * | 12/1986 | Kanno | A61M 5/344 285/332 |
| 6,286,651 B1 | * | 9/2001 | Mazziotti | F16B 39/34 192/110 R |
| 2004/0226332 A1 | * | 11/2004 | Bryan | B21D 26/033 72/62 |
| 2012/0063863 A1 | * | 3/2012 | Campau | F16B 39/20 411/317 |
| 2015/0094654 A1 | | 4/2015 | Bansal et al. | |

FOREIGN PATENT DOCUMENTS

| | | | |
|---|---|---|---|
| JP | H1061634 A | * | 3/1998 |
| WO | 2009142120 A1 | | 11/2009 |
| WO | 2011142142 A1 | | 11/2011 |

\* cited by examiner

MECHANISM FOR CONTROLLING UNINTENTIONAL MOVEMENT OF COMPONENTS

FIELD OF THE DISCLOSURE

The present disclosure relates generally to medical devices that are used in the human body. In particular, in many embodiments, the present disclosure relates to a friction member positioned between two threadably engaged components to assist in controlling and/or limiting unintentional and/or undesirable rotational movement of the threadably engaged components with respect to one another. In some embodiments, the threadably engaged components are part of a resistance assembly for holding a medical device actuator in a particular position and/or to improve the ease of which the activator moves into one position versus another position.

BACKGROUND

Medical devices, such as catheter systems, are well known in the art for use in medical procedures, such as diagnostic, therapeutic and ablative procedures. Typical catheter systems generally include an elongate flexible catheter shaft extending from a handle. A physician manipulates the catheter shaft through the patient's vasculature to an intended site within the patient.

The catheter system may be comprised of multiple components and may include mechanical steering features or components that may be manually manipulated to position a catheter shaft within the body at a desired site or to operate the catheter system during use. Individual components of a catheter system may be integrally formed into a unitary member, separately formed and permanently affixed to one another, or separately formed and releasably secured to one another. Other configurations may also be known in the art.

A catheter or catheter system may be positioned within a patient's vasculature during a procedure by simultaneous application of torque at the proximal end of the catheter and/or by selectively deflecting the distal tip of the catheter in a desired direction. The distal tip of the catheter can be deflected by a pull wire or other suitable tension member attached or anchored at the distal end of the catheter and extending proximally to an actuator in a control handle that controls the application of tension on the pull wire. In some cases, movement of the actuator and rotation of the catheter system at a proximal end thereof, however, may potentially cause unintended and/or undesirable rotation of certain releasably secured components with respect to one another.

BRIEF SUMMARY OF THE DISCLOSURE

In one embodiment, the present disclosure is directed to a medical device. The medical device comprises a first threaded component, a second threaded component coupled to the first threaded component, and a friction member positioned between the first threaded component and the second threaded component. The friction member is sized and configured to provide a frictional resistance between the first threaded component and the second threaded component when the first threaded component and the second threaded component are rotated with respect to one another.

In another embodiment, the present disclosure is directed to a medical device comprising a catheter shaft having a proximal end and a deflectable distal region, a handle coupled to the proximal end of the catheter shaft, wherein the handle includes an actuator movable relative to the handle along a longitudinal axis, and a resistance assembly positioned adjacent the actuator. The resistance assembly comprises a handle cap threadably coupled to a threaded portion located on a distal end of the handle, a compression ring positioned around the actuator and within the handle cap, and a friction member positioned between the handle cap and the threaded portion of the handle. The friction member is sized and configured to provide a frictional resistance between the handle cap and the threaded portion of the handle when the handle cap and the handle are rotated with respect to one another.

In another embodiment, the present disclosure is directed to a method of adjusting a medical device. The method comprises providing a medical device comprising a first threaded component, a second threaded component coupled to the first threaded component, and a friction member positioned between the first threaded component and the second threaded component; and rotating the first threaded component with respect to the second threaded component with sufficient force to overcome the frictional resistance imparted by the friction member.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings. It is understood that that Figures are not necessarily to scale.

DETAILED DESCRIPTION OF THE DISCLOSURE

The present disclosure provides a catheter system suitable for use in the human vasculature for known medical procedures. Catheter systems of the multiple embodiments of the present disclosure exhibit an increased resistance to unintentional and/or undesirable rotational movement between various components that are releasably secured to one another; that is, the present disclosure provides embodiments of catheter systems wherein unintended rotational movement between two components is minimized or eliminated. Such embodiments may lead to more consistent and improved patient outcomes. For purposes of this description, the present disclosure will be described in connection with numerous embodiments of a plunger-type catheter including a resistance assembly. It is contemplated, however, that the described features and methods of the present disclosure as described herein may be incorporated into any number of catheters (e.g., steerable catheters, introducer catheters, balloon catheters, bullet catheters, and the like) or other medical devices as would be appreciated by one of ordinary skill in the art based on the disclosure herein.

More specifically, some embodiments of the present disclosure provide a catheter system including a first threaded component and a second threaded component releasably secured to one another and a friction member positioned therebetween. In many embodiments, the friction member is comprised of a thermoplastic material, and is in the form of a block, plug, ring, overlay or the like that is optionally secured to the exterior surface of a threaded portion of the first or second threaded component.

The friction member as described herein provides an increased frictional resistance to rotation of the second threaded component with respect to the first threaded component (and vice versa) such that an additional force is needed to rotate the first and second threaded components with respect to each other as compared to threaded components without a friction member positioned therebetween. This increased frictional resistance may reduce the potential for unintentional and/or undesirable movement between the first and second threaded components during use of the catheter system; that is, as some catheter systems include separate components that are releasably secured to one another, for example by compatible threaded sections located on each component, a user may potentially in some cases unintentionally cause the sections to rotate with respect to each other thus causing the connection therebetween to either tighten or loosen from its original or desired position. As rotational movement relative to one another may potentially impact the performance of other components in the catheter system, or the catheter system overall, it may be desired in some cases to provide an apparatus and method to assist in limiting the potential for such unintentional and/or undesirable rotational movement of the releasably secured components with respect to one another.

Figure 1:
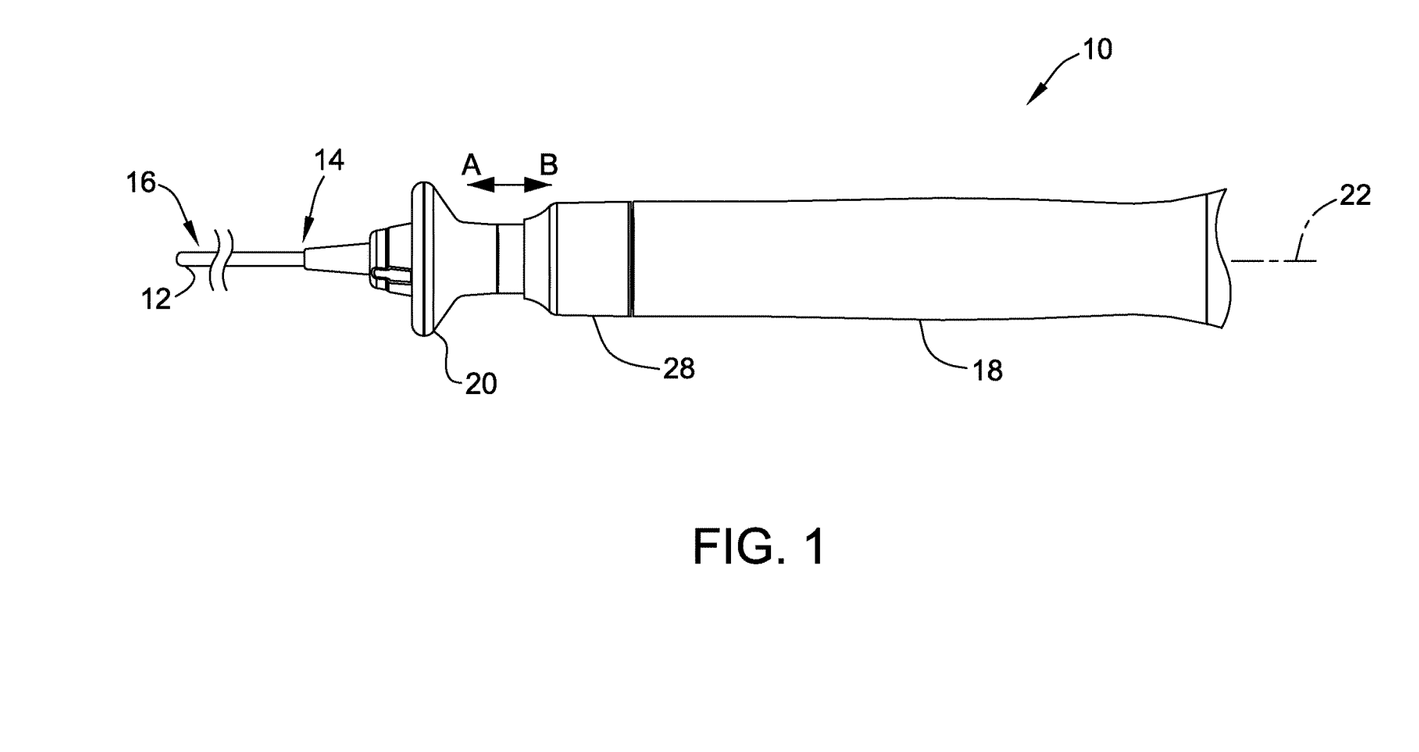
FIG. 1 is a perspective view of one embodiment of a catheter system including a handle, a catheter shaft, an actuator, and a resistance assembly.

Referring now to the drawings, and specifically to FIG. 1, there is shown a plunger-type catheter 10 in an undeflected, or neutral position. Catheter 10 generally includes an elongate body 12, having a proximal end 14 and a deflectable distal region 16, and a handle 18 attached to proximal end 14 of elongate body 12. Handle 18 includes an actuator 20. As illustrated in FIG. 1, actuator 20 is a plunger that is moveable relative to handle 18 along a longitudinal axis 22 of handle 18 in a first direction along arrow A (e.g., distally) that effects deflection of distal region 16 from the neutral position, as well as in a second, opposite direction along arrow B (e.g., proximally) that effects return of distal region 16 toward the neutral position. For example, catheter 10 can be of the type disclosed in U.S. Provisional Application No. 61/884,897, filed Sep. 30, 2013, which is hereby incorporated by reference as though fully set forth herein.

Figure 2:
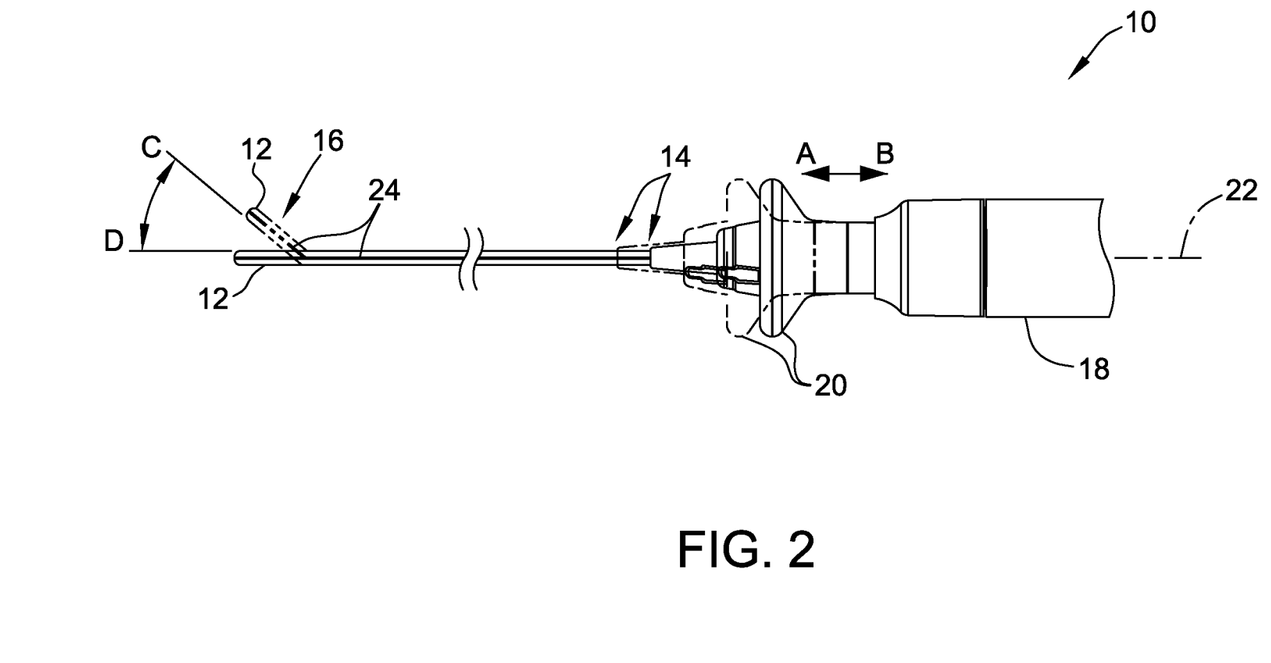
FIG. 2 illustrates the use of a pull wire to deflect the distal end of the catheter shaft of FIG. 1.

FIG. 2 illustrates the use of a pull wire 24 for deflecting distal region 16 of catheter 10. Pull wire 24 extends through elongate body 12. Pull wire 24 is coupled to distal region 16 of elongate body 12, such that movement of actuator 20 in the first direction along arrow A effects deflection of distal region 16 from the neutral position along a first deflection direction (e.g., arrow C), and such that movement of actuator 20 in the second direction along arrow B effects the return of distal region 16 towards the neutral position (e.g., along arrow D). Insofar as a person of ordinary skill in the art will appreciate the use of pull wires in a catheter, a detailed explanation of this aspect of the disclosure is not provided herein.

Although the catheter systems disclosed herein are described primarily with respect to unidirectional catheters, it should be recognized that the disclosed principles are equally applicable in other contexts, including but not limited to, bidirectional catheters. That is, for example, movement of actuator 20 in the first direction along arrow A could effect deflection of distal region 16 from the neutral position in a first deflection direction (e.g., arrow C in FIG. 2), while movement of actuator 20 in the second direction could effect deflection of distal region 16 from the neutral position in a second deflection direction, with both the first deflection direction and second deflection direction lying in the same plane.

Catheter 10 of FIGS. 1 and 2 may further include a resistance assembly configured to make movement of actuator 20 in a first direction along arrow A relatively easier than movement of actuator 20 in a second direction along arrow B, no matter what sort of movement distal region 16 is effected thereby (e.g., whether deflection from neutral or return to neutral). That is, the resistance assembly may make it relatively easier for a practitioner to move actuator 20 into a first position along arrow A and relatively harder for a practitioner to move actuator 20 into a second position along arrow B. Typically, the force exerted by the resistance assembly is a frictional force arising between actuator 20 and the resistance assembly. That is, the resistance assembly provides a normal force and a frictional resistance against the movement of actuator 20 relative to handle 18 that differs depending on the direction in which actuator 20 is moving.

Figure 3:
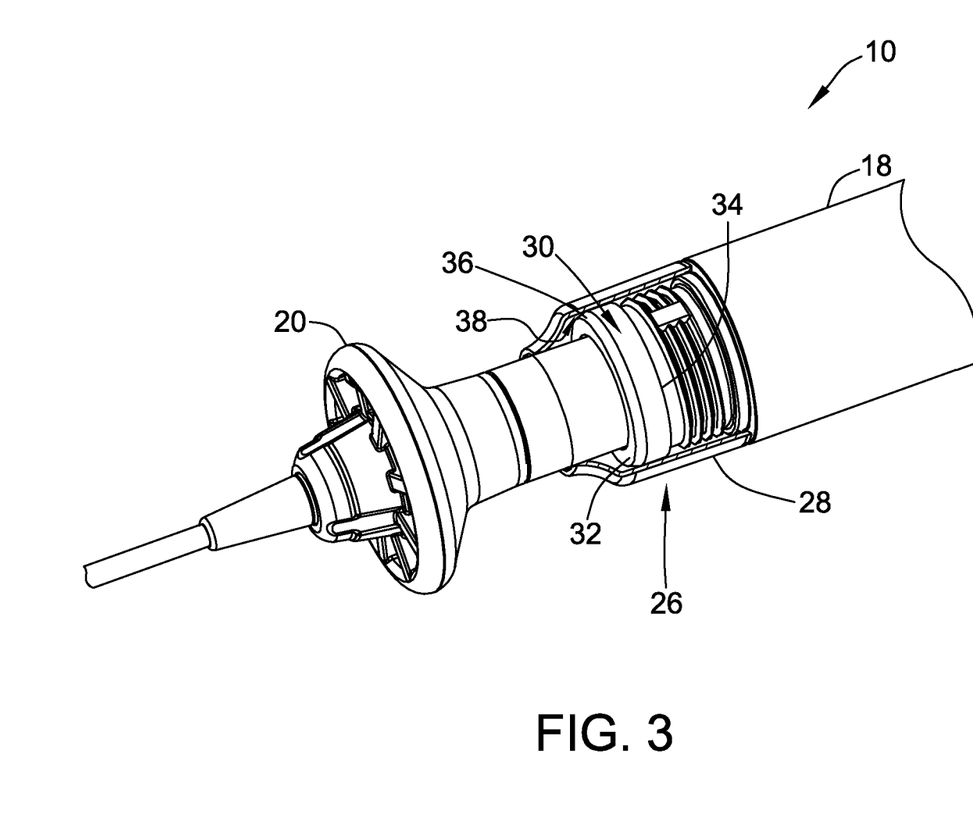
FIG. 3 is a cut-away view of the catheter system of FIG. 1 illustrating a cross-section of the resistance assembly.

FIG. 3 illustrates a cross-section of an exemplary resistance assembly for use in catheter 10. Resistance assembly 26 is positioned adjacent actuator 20 and includes a handle cap 28 and a compression ring 30, Compression ring 30 is positioned within handle cap 28 and around actuator 20 and includes a first surface 32 and a second opposite surface 34. In one particular embodiment, first surface 32 includes a chamfer 36, while second surface 34 is generally flat (i.e., generally follows the profile of handle cap 28). Chamfer 36 forms a cavity 38 in first surface 32 such that there is a greater distance between first surface 32 and handle cap 28 than between second surface 34 and handle cap 28.

First surface 32 is oriented in the direction where the lower resistance to movement of actuator 20 is desired, e.g., in the first or distal direction (along arrow A as shown in FIGS. 1 and 2) that effects deflection of distal region 16 from neutral. Thus, as actuator 20 is driven in the first direction along arrow A, compression ring 30 deforms into the space created by chamfer 36 (i.e., cavity 38), thereby reducing both the normal force that compression ring 30 exerts on actuator 20 and the frictional resistance to movement of actuator 20 in the first direction. Conversely, when actuator 20 is driven in the second direction along arrow B (as shown in FIGS. 1 and 2), compression ring 30 is driven against handle cap 28, increasing both the normal force that compression ring 30 exerts on actuator 20 and the frictional resistance to movement of actuator 20 in the second position. As a result, it is relatively easier for a practitioner to move actuator 20 through resistance assembly 26 in the first direction along arrow A than in the second direction along arrow B. Resistance assembly 26 may also provide an added frictional resistance to any internally-arising restorative forces that could tend to move distal region 16 towards neutral (e.g., spring forces arising when pull wire 24 is placed in tension via the movement of actuator 20 in the direction of arrow A). In this regard, resistance assembly 26 can also be regarded as a self-locking assembly for catheter 10.

Compression ring 30 may be formed from any suitable materials such that compression ring 30 is configured to provide the characteristics thereof set forth in the present disclosure. In some embodiments of the present disclosure, compression ring 30 is formed of silicone, polytetrafluoroethylene, polyurethane, copolymers of hexafluropropylene and vinylidene fluoride, or combinations thereof. In one particular embodiment of the present disclosure, compression ring 30 is formed of about 85% by weight silicon and about 15% by weight polytetrafluoroethylene.

Compression ring 30 may be of any size such that it is configured to provide the characteristics thereof set forth in the present disclosure. In some embodiments of the present disclosure, compression ring has an inner diameter of from about 0.450 inches (about 1.143 centimeters) to about 0.550 inches (about 1.397 centimeters), including from about 0.500 inches (about 1.27 centimeters) to about 0.505 inches (about 1.2827 centimeters), and including about 0.502 inches (about 1.275 centimeters). Further, in some embodiments of the present disclosure, compression ring 30 may have an outer diameter of from about 0.650 inches (about 1.651 centimeters) to about 0.700 inches (about 1.778 centimeters), including from about 0.685 inches (about 1.7399 centimeters) to about 0.690 inches (about 1.7526 centimeters), including about 0.688 inches (about 1.7475 centimeters).

In one embodiment, handle cap 28 is releasably secured to handle 18 via compatible threads positioned on each of an external surface of handle 18 and an internal surface of handle cap 28. By releasably securing handle cap 28 to handle 18, as opposed to permanently fixing these components together, resistance assembly 26 is configured such that it is adjustable based on the desired amount of friction and/or normal force acting against actuator 20 by compression ring 30. That is, as shown in FIGS. 4 and 5, the amount of compression imparted to compression ring 30 is dependent upon the position of handle cap 28 with respect to a distal end 40 of handle 18.

Figure 4:
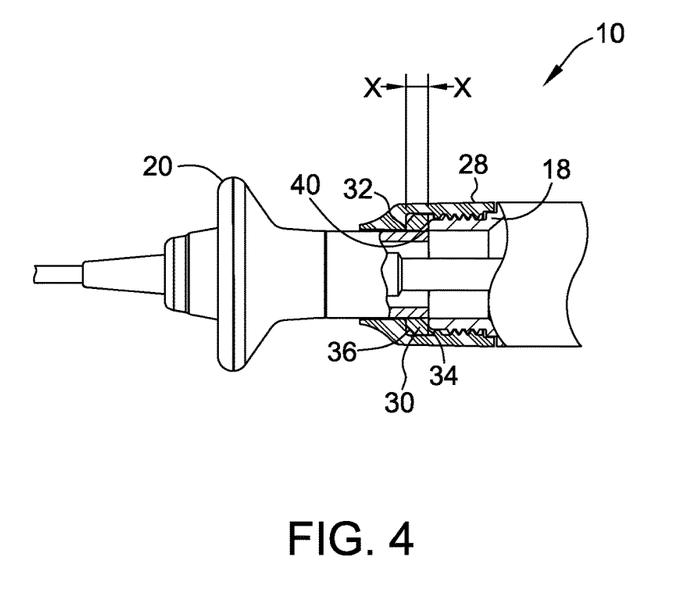
FIG. 4 is a cross-sectional view of the catheter system of FIG. 1 illustrating the resistance assembly in a first position.

FIG. 4 illustrates handle cap 28 in a first position relative to handle 18, and in particular distal end 40 of handle 18. Rotating handle cap 28 clockwise repositions, or tightens, the connection between handle cap 28 and handle 18 from the first position shown in FIG. 4 to a second position shown in FIG. 5, and thus causes an increased compressive force acting on first surface 32 and second surface 34 of compression ring 30. This increased compressive force causes compression ring 30 to become narrower along dimension X-X as shown in FIG. 5 and also causes an increase in the frictional resistance to movement of actuator 20 and the normal force exerted on actuator 20. In other words, by rotating handle cap 28 with respect to handle 18, and thus adjusting the position of handle cap 28 with respect to handle 18, the functionality of resistance assembly 26 as an auto-locking assembly can be altered or repositioned as desired.

Figure 5:
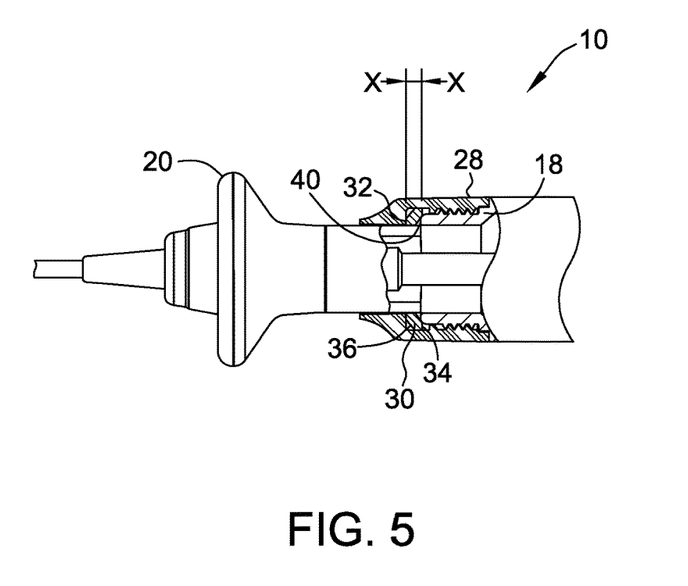
FIG. 5 is a cross-sectional view of the catheter system of FIG. 1 illustrating the resistance assembly in a second position.
Figure 6:
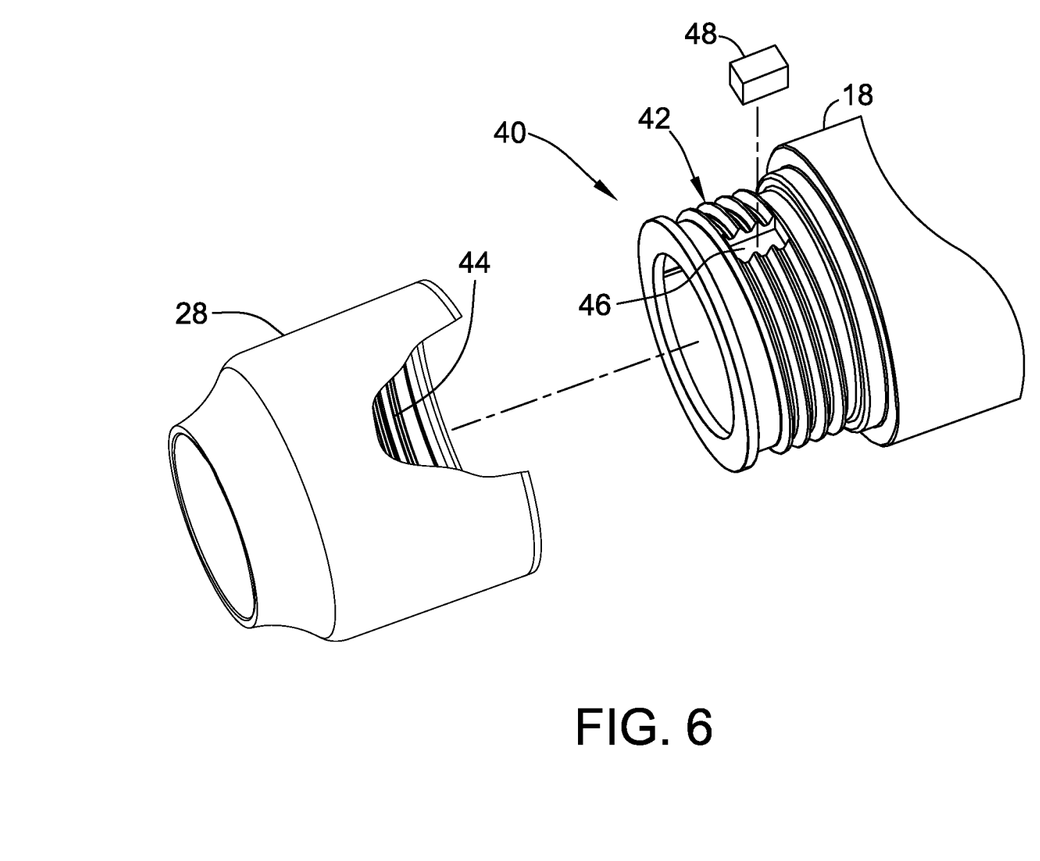
FIG. 6 is an exploded view of a handle cap, handle, and friction her according to one embodiment of the present disclosure.

In accordance with the present disclosure, in many embodiments, resistance assembly 26 as shown in FIGS. 3-5 may further include a friction member positioned between a threaded portion of handle 18 and a threaded portion of handle cap 28 to assist in controlling and/or limiting unintentional and/or undesirable rotational movement of handle cap 28 with respect to handle 18. In one embodiment, as illustrated in FIG. 6, distal end 40 of handle 18 includes a threaded portion 42 configured to threadably engage a threaded portion 44 of handle cap 28. A pocket 46 is formed within threaded portion 42 of handle 18 (i.e., on an exterior surface of distal end 40 of handle 18) and is sized and configured to receive friction member 48 therein and thus limit the movement of friction member 48 about the exterior surface of handle 18 when handle cap 28 is rotated relative thereto.

Pocket 46 may be substantially rectangular shaped, as shown in FIG. 6, or may have any other shape and size substantially corresponding to a cross-sectional shape and size of a friction member to be positioned therein such that the friction is increased between handle cap 28 and handle 18; that is, pocket 46 may be oval, triangular, circular, square, irregular shaped, etc. in some embodiments, pocket 46 may have a length that extends along substantially the entire longitudinal length of threaded portion 42 such that all threads include a portion of pocket 46 (as shown in FIG. 6) or may be positioned at least partially within the outermost ends of threaded portion 42 such that at least one thread does not include any portion of pocket 46.

Further, in some embodiments, pocket 46 may have a width of from about 0.050 inches (0.127 centimeters) to about 0.150 inches (about 0.381 centimeters), including from about 0.075 inches (about 0.1905 centimeters) to about 0.10 inches (about 0.254 centimeters), and including about 0.091 inches (about 0.2311 centimeters). Pocket 46 may, in some embodiments, have a depth extending from the outermost portion of threaded portion 42 to the innermost portion of pocket 46 of from about 0.050 inches (about 0.127 centimeters) to about 0.070 inches (about 0.1778 centimeters), including from about 0.056 inches (about 0.1422 centimeters) to about 0.060 inches (about 0.1524 centimeters), including about 0.058 inches (about 0.1473 centimeters).

Figure 7:
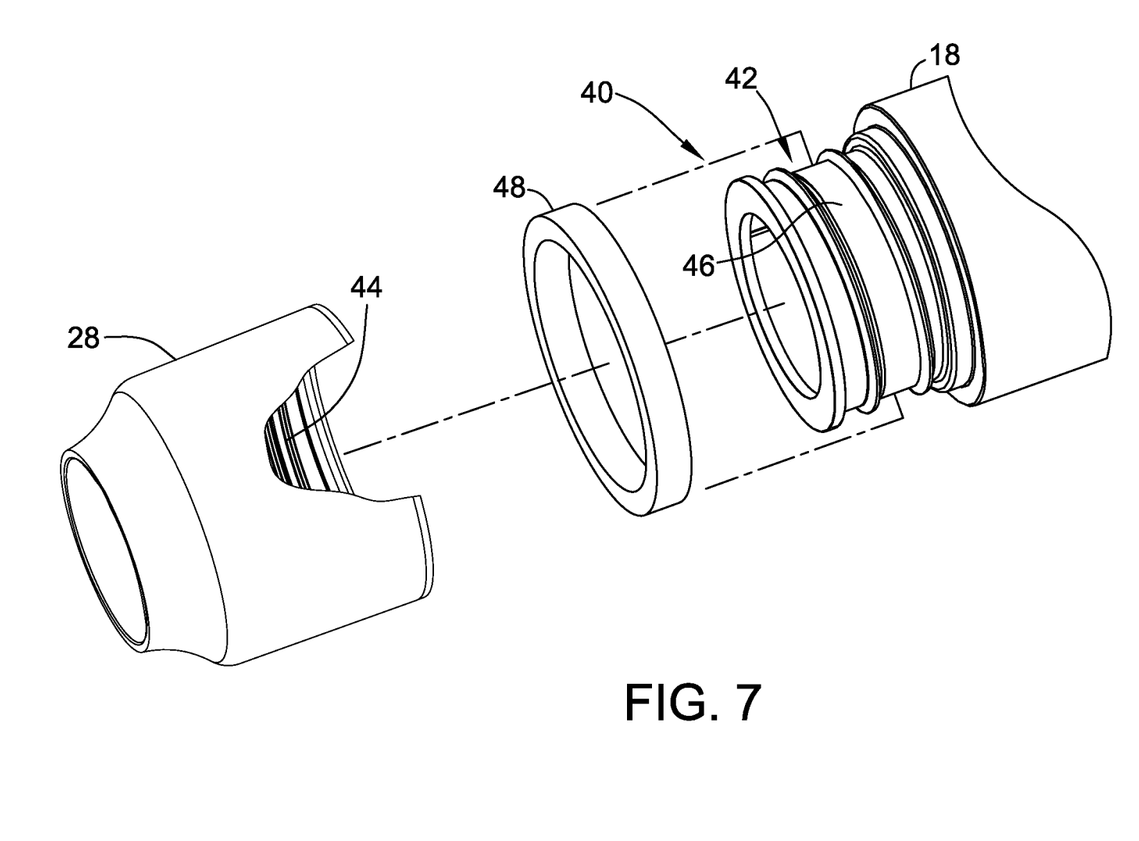
FIG. 7 is an exploded view of a handle cap, handle, and friction member according to another embodiment of the present disclosure.

In another embodiment of the present disclosure, as shown in FIG. 7, pocket 46 may substantially encircle an exterior circumference of handle 18 within threaded portion 42 such that handle 18 and handle cap 28 may still be threadably engaged while having increased friction.

Figure 8:
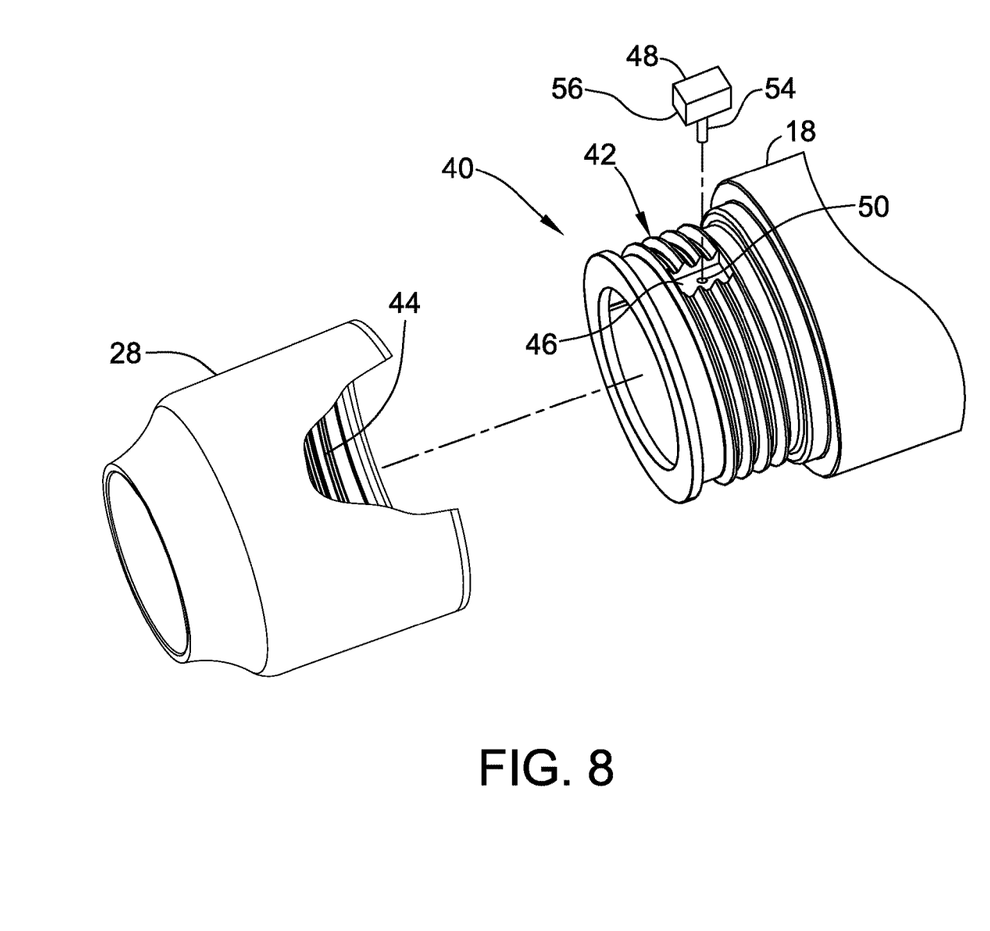
FIG. 8 is an exploded view of a handle cap, handle, and friction member according to another embodiment of the present disclosure.

In another embodiment of the present disclosure, as shown in FIG. 8, pocket 46 may include a bore 50 extending from the exterior surface of handle 18 to the interior surface of handle 18 for receiving a securement member 54 of friction member 48 (discussed in more detail below). One skilled in the art will appreciate that bore 50 may extend completely through the wall of handle 18 or may extend only partially through handle 18 so as to be configured to cooperate with securement member 54 of friction member 48. In another embodiment, shown in FIG. 9, bore 50 includes threads 52 configured to engage securement member 54 of friction member 48.

Figure 9:
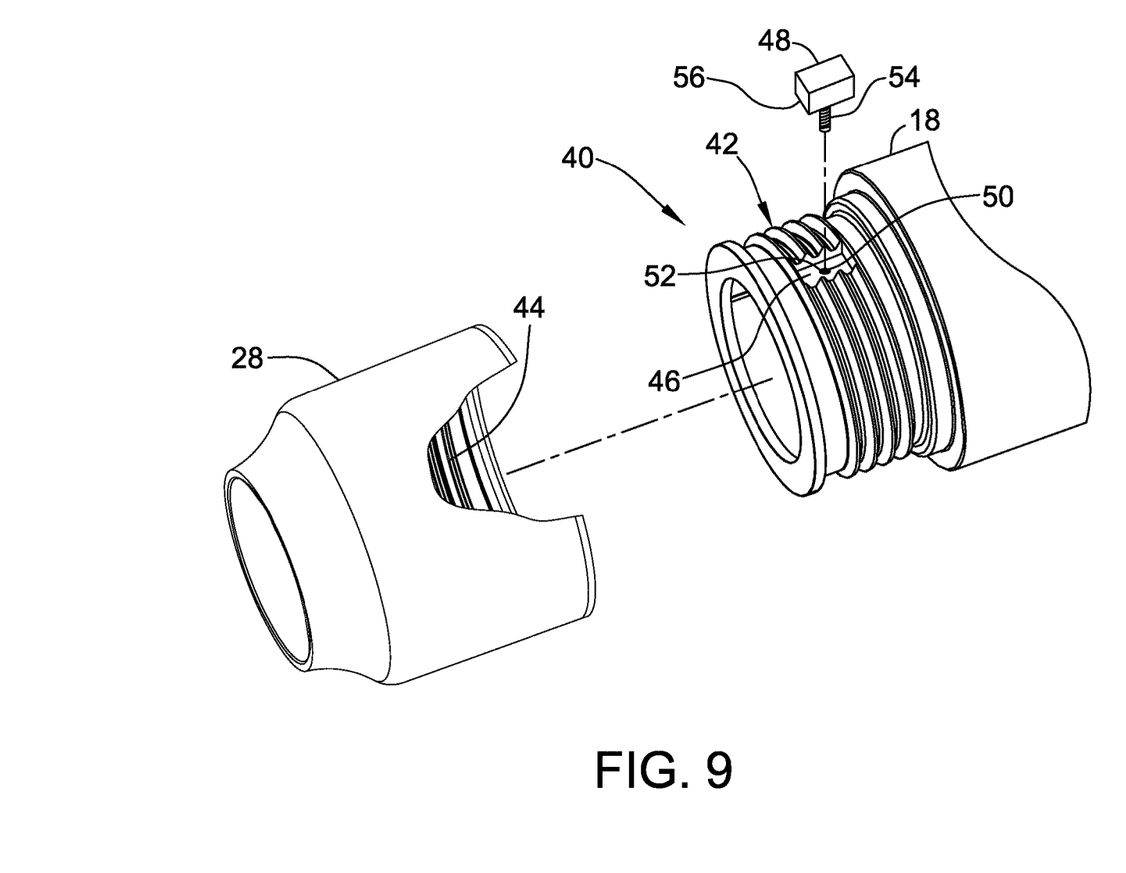
FIG. 9 is an exploded view of a handle cap, handle and friction member according to another embodiment of the present disclosure.
Figure 10:
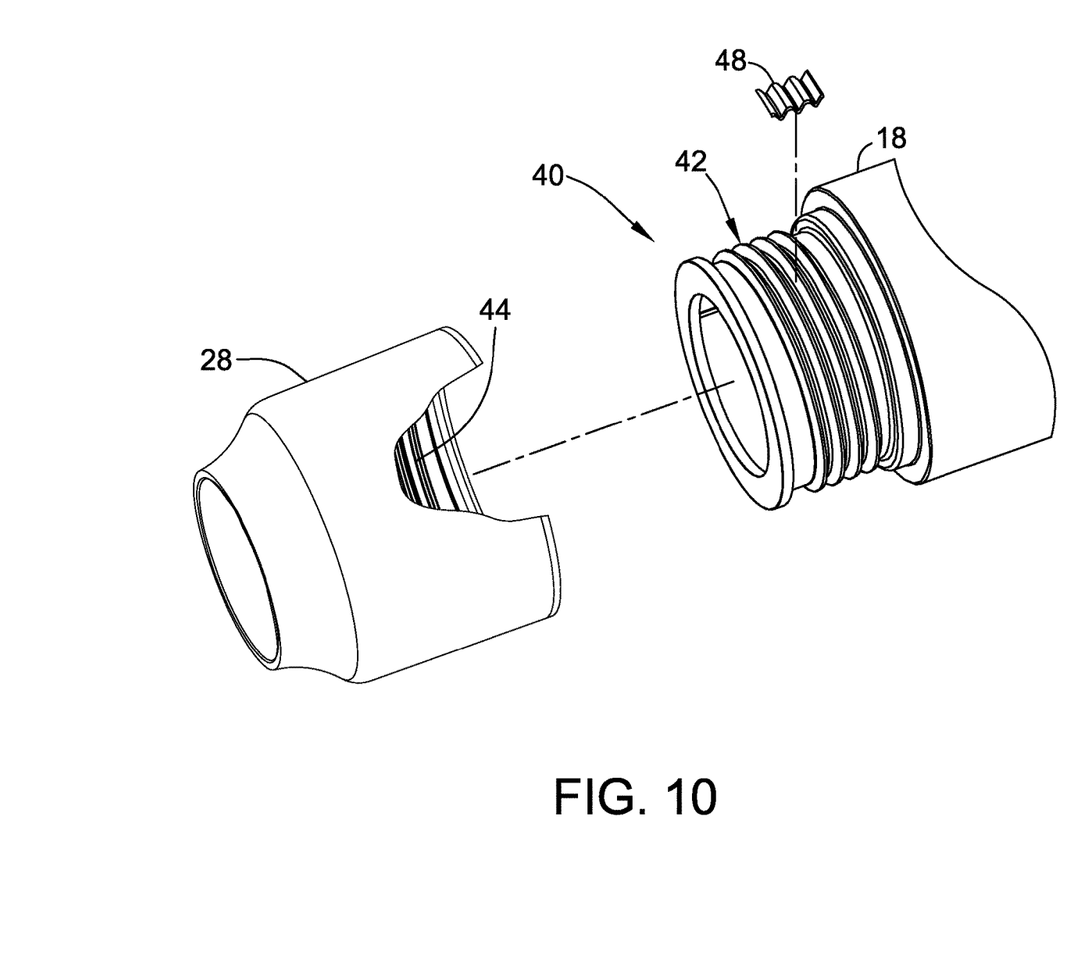
FIG. 10 is an exploded view of a handle cap, handle and friction member according to another embodiment of the present disclosure.

As noted above, friction member 48 may have a rectangular shape as shown in FIG. 6 substantially corresponding in size and shape to pocket 46, or may have any other size and shape such that it is configured to be received within pocket 46. For example, in one embodiment as illustrated in FIG. 7, friction member 48 may be a substantially flat ring sized and configured to be received within pocket 46 extending substantially circumferentially about handle 18. In another embodiment, as shown in FIGS. 8 and 9, friction member 48 may include a securement member 54 extending from a bottom surface 56 of friction member 48 and sized and configured to be received within bore 50. Securement member 54 may have a substantially flat surface as shown in FIG. 8 or may include threads configured to engage threads 52 of bore 50 as shown in FIG. 9. Securement member 54 may be formed integrally with friction member 48 or may be formed separately from friction member 48 and secured thereto via a suitable adhesive or other contact agent, threads, or any other suitable means, in yet another embodiment, friction member 48 may be sized and configured to be positioned to overlie a portion of threaded portion 42 on handle 18 as illustrated in FIG. 10.

Friction member 48 may be secured to handle 18 in any manner suitable such that friction member 48 remains relatively securely in place with respect to handle 18 upon rotation of handle cap 28, thus creating an increased frictional resistance to rotation between handle cap 28 and handle 18. In one embodiment, friction member 48 may be received within pocket 46, which limits potential movement of friction member 48 upon rotation of handle cap 28 with respect to handle 18 (see FIGS. 6 and 7). In another embodiment, friction member 48 may be adhered to pocket 46 or directly to threaded portion 42 of handle 18 with any suitable adhesive or contact agent known in the art capable of providing a suitable bond therebetween. In yet another embodiment, friction member 48 may be secured to handle 18 via securement member 54 positioned through or within bore 50 (see FIGS. 8 and 9). As will be appreciated by one skilled in the art, the means for attaching or securing friction member 48 to handle 18 is not critical, and may be accomplished by any one of the methods disclosed herein, or by a combination of two or more of the methods disclosed herein, or by other methods, without departing from the scope of the present disclosure.

Friction member 48 may be suitably sized and configured and formed of any suitable pliable material capable of deforming between threaded portion 42 of handle 18 and threaded portion 44 of handle cap 28 and causing an increase in the frictional resistance to rotation therebetween as described herein. For example, in one embodiment, friction member 48 may be formed from a thermoplastic material or combination of thermoplastic materials. Desirable materials may include, but are not limited to, silicone, polyurethane, polytetrafluoroethylene, and combinations thereof. In one specific embodiment, friction member 48 is constructed from silicone, such as 90 Shore A Durometer silicone. Further, in some embodiments, all or a portion of one or more surfaces of friction member 48 may include a treatment or finish, such as fish scaling or bumps, that yields an additional frictional resistance to rotation of handle cap 28 with respect to handle 18.

In use, catheter 10 (as shown in FIGS. 1 and 2) is inserted within the vasculature of a patient until a desired location or position of distal region 16 is obtained within the patient. Actuator 20 may be moved between two positions, i.e., along arrows A and B as shown in FIG. 2, to cause distal region 16 of elongate body 12 to deflect to a desired position. Movement of actuator 20 by a user, however, may cause unintentional and/or undesirable rotational movement of handle cap 28 with respect to handle 18. This rotational movement may alter the compression applied to compression ring 30 between handle cap 28 and handle 18 thus reducing the self-locking characteristic of resistance assembly 26. By including friction member 48 between handle cap 28 and handle 18, the potential of unintentional and/or undesirable rotation between handle cap 28 handle 18 during ordinary use of catheter 10 is at least partially reduced. That is, by positioning friction member 48 between threaded portion 42 of handle 18 and threaded portion 44 of handle cap 28, an increased force is needed to rotate handle cap 28 relative to handle 18, thus reducing the possibility that handle cap 28 could rotate unintentionally during use of catheter 10. Further, because handle cap 28 and handle 18 are releasably secured to one another, resistance assembly 26 remains adjustable if an increase or decrease in frictional resistance and/or normal force on actuator 20 is desired.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A medical device comprising:
    a first threaded component comprising a plurality of threads on an exterior surface thereof;
    a second threaded component coupled to the first threaded component; and
    a friction member positioned between an externally threaded portion of the first threaded component and an internally threaded portion of the second threaded component and secured to the first threaded component, wherein the friction member is sized and configured to provide a frictional resistance between the first threaded component and the second threaded component when the first threaded component and the second threaded component are rotated with respect to one another, and wherein the friction member comprises a securement member having threads formed thereon,
    wherein the first threaded component further comprises a pocket formed within the exterior surface thereof and a bore extending from the exterior surface to an interior surface thereof, the bore comprising threads, wherein the pocket has a length that extends across an entirety of two or more of the plurality of threads of the first threaded component and is configured to receive the friction member therein such that the friction member extends across the entirety of the two or more of the plurality of threads of the first threaded component to inhibit unintentional rotation of the first threaded component relative to the second threaded component, wherein the bore is configured to receive the securement member therein, and the threads of the bore are configured to engage the threads of the securement member of the friction member.

2. The medical device of claim 1 wherein the second threaded component comprises threads on an interior surface thereof.

3. The medical device of claim 2 wherein the friction member is adhered to the pocket of the first threaded component.

4. The medical device of claim 3 wherein the friction member is comprised of a material selected from the group consisting of silicone, polyurethane, or polytetrafluoroethylene.

5. The medical device of claim 1 wherein each of the pocket and the friction member have a rectangular cross-section.

6. The medical device of claim 1 wherein the plurality of threads extend from a first longitudinal position to a second longitudinal position, and wherein the pocket extends substantially from the first longitudinal position to the second longitudinal position.

7. The medical device of claim 1 wherein the friction member is comprised of a thermoplastic material.

8. The medical device of claim 1 wherein at least a portion of the friction member comprises a surface treatment finish.

9. A medical device comprising:
   a catheter shaft having a proximal end and a deflectable distal region;
   a handle coupled to the proximal end of the catheter shaft, wherein the handle includes an actuator movable relative to the handle along a longitudinal axis and a threaded portion including a plurality of threads on an exterior surface thereof, the threaded portion located on a distal end of the handle; and
   a resistance assembly positioned adjacent the actuator, wherein the resistance assembly comprises:
      a handle cap threadably coupled to the threaded portion of the handle;
      a compression ring positioned around the actuator and within the handle cap; and
      a friction member positioned between an internally threaded portion of the handle cap and the threaded portion of the handle, wherein the friction member is sized and configured to provide a frictional resistance between the handle cap and the threaded portion of the handle when the handle cap and the handle are rotated with respect to one another, and wherein the friction member comprises a securement member having threads formed thereon,
   wherein the threaded portion of the handle further comprises a pocket formed within the exterior surface thereof and a bore extending from the exterior surface to an interior surface thereof, the bore comprising threads, wherein the pocket has a length that extends across an entirety of two or more of the plurality of threads of the threaded portion of the handle and is configured to receive the friction member therein such that the friction member extends across the entirety of the two or more of the plurality of threads of the threaded portion of the handle to inhibit unintentional rotation of the handle cap relative to the threaded portion of the handle, wherein the bore is configured to receive the securement member therein, and the threads of the bore are configured to engage the threads of the securement member of the friction member.

10. The medical device of claim 9 wherein the handle cap comprises threads on an interior surface thereof.

11. The medical device of claim 9 wherein the friction member is adhered to the exterior surface of the handle.

12. A method of adjusting a medical device, the method comprising:
   providing a medical device comprising a first threaded component, a second threaded component coupled to the first threaded component, and a friction member positioned between the first threaded component and the second threaded component, wherein the friction member includes a securement member having threads formed thereon, wherein the first threaded component includes (i) a plurality of threads on an exterior surface thereof, (ii) a pocket formed within an exterior surface thereof, and (iii) a bore extending from the exterior surface to an interior surface thereof, the bore including threads, wherein the pocket has a length that extends across an entirety of two or more of the plurality of threads of the first threaded component and is configured to receive the friction member therein such that the friction member extends across the entirety of the two or more of the plurality of threads of the first threaded component to inhibit unintentional rotation of the first threaded component relative to the second threaded component, wherein the bore is configured to receive the securement member therein, and the threads of the bore are configured to engage the threads of the securement member of the friction member; and
   rotating the first threaded component with respect to the second threaded component with sufficient force to overcome the frictional resistance imparted by the friction member.

* * * * *